US00PP35321P2

(12) United States Plant Patent
Shafer

(10) Patent No.: US PP35,321 P2
(45) Date of Patent: Aug. 15, 2023

(54) ***PETUNIA* PLANT NAMED 'BALSURSRE'**

(50) Latin Name: ***Petunia* x *hybrida***
Varietal Denomination: Balsursre

(71) Applicant: Ball Horticultural Company, West Chicago, IL (US)

(72) Inventor: Gail Shafer, Santa Maria, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/099,709

(22) Filed: Jan. 20, 2023

(51) Int. Cl.
*A01H 5/02* (2018.01)
*A01H 6/82* (2018.01)

(52) U.S. Cl.
USPC ..... Plt./356.23

(58) Field of Classification Search
USPC ..... Plt./356.1, 356.23
See application file for complete search history.

*Primary Examiner* — Susan McCormick Ewoldt
(74) *Attorney, Agent, or Firm* — Audrey Charles

(57) ABSTRACT

A new and distinct cultivar of *Petunia* plant named 'Balsursre', characterized by its medium red-colored flowers, medium green-colored foliage, and moderately vigorous, mounded-trailing growth habit, is disclosed.

1 Drawing Sheet

Latin name of genus and species of plant claimed: *Petunia* x *hybrida*.

Variety denomination: 'Balsursre'.

BACKGROUND OF THE INVENTION

The present invention relates to a new and distinct cultivar of *Petunia* plant botanically known as *Petunia* x *hybrida* and hereinafter referred to by the cultivar name 'Balsursre'.

The new cultivar originated in a controlled breeding program in Arroyo Grande, Calif. during May 2018. The objective of the breeding program was the development of *Petunia* cultivars that have a mounded-trailing growth habit suitable for hanging basket, pot plant, and landscape use.

The new *Petunia* cultivar is the result of cross-pollination. The female (seed) parent of the new cultivar is the proprietary *Petunia* x *hybrida* breeding selection coded PET-00292-01, not patented, characterized by its medium red-colored flowers, medium green-colored foliage, low growth vigor, and compact, mounded growth habit. The male (pollen) parent of the new cultivar is the proprietary *Petunia* x *hybrida* breeding selection coded PET-00274-04, not patented, characterized by its medium purple-colored flowers, medium green-colored foliage, and moderately vigorous, spreading growth habit. The new cultivar was selected as a single flowering plant within the progeny of the above stated cross-pollination during April 2019 in a controlled environment in Arroyo Grande, Calif.

Asexual reproduction of the new cultivar by terminal stem cuttings since April 2019 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsursre' as a new and distinct cultivar of *Petunia* plant:

1. Medium red-colored flowers;
2. Medium green-colored foliage; and
3. Moderately vigorous, mounded-trailing growth habit.

Plants of the new cultivar differ from plants of the female parent primarily in having increased growth vigor and a more trailing growth habit. Plants of the new cultivar differ from plants of the male parent primarily in having medium red-colored flowers that are different from the medium purple-colored flowers of the male parent and a more mounded growth habit.

Of the many commercially available *Petunia* cultivars, the most similar in comparison to the new cultivar is SureShot Dark Red 'Balsursared', not patented. However, in side-by-side comparison, plants of the new cultivar differ from plants of 'Balsursared' in at least the following characteristics:

1. Plants of the new cultivar have a lighter red flower color than plants of 'Balsursared';
2. Plants of the new cultivar have less growth vigor than plants of 'Balsursared'; and
3. Plants of the new cultivar have larger flowers than plants of 'Balsursared'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balsursre'. The plants were approximately 11-weeks old. The plants were grown in 6-inch containers for approximately 8 weeks in a greenhouse in West Chicago, Ill. Plants were given one pinch three weeks after transplant.

DETAILED BOTANICAL DESCRIPTION

Figure 1:
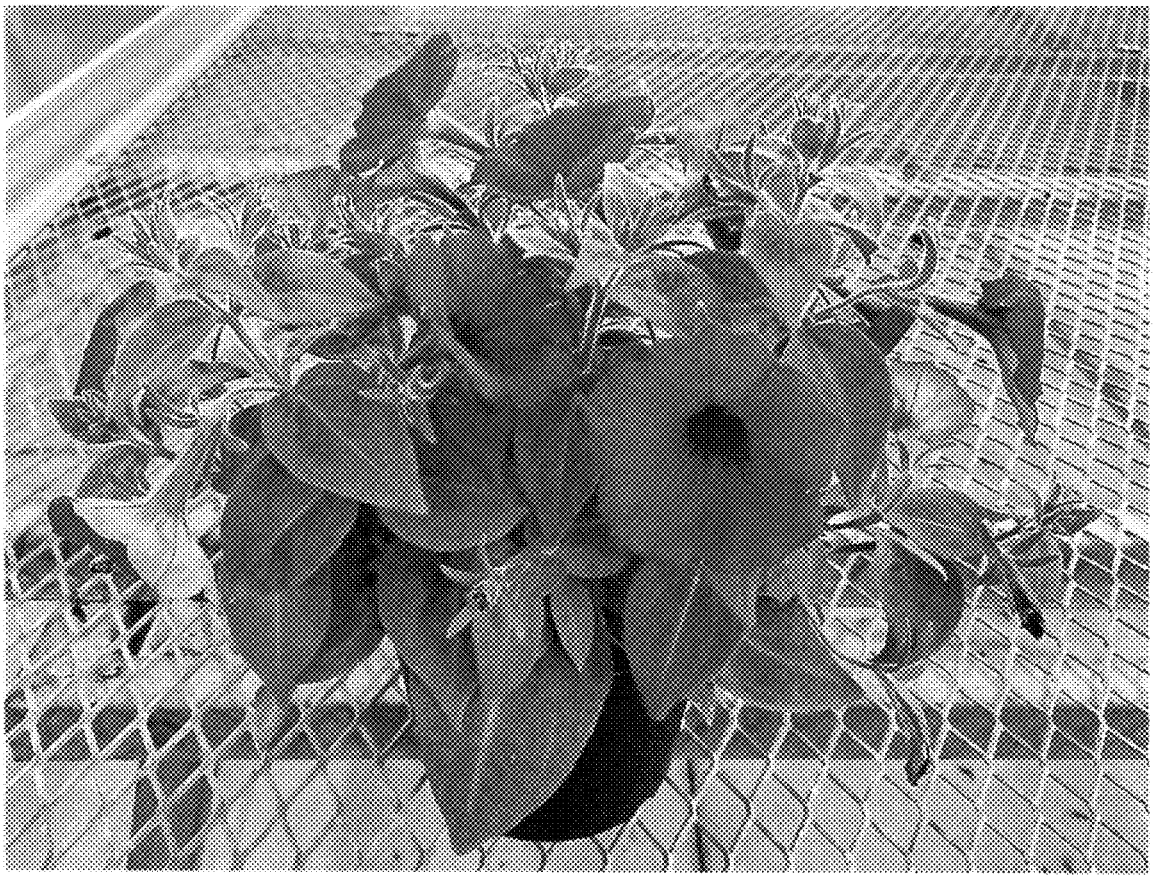
FIG. 1 illustrates a side view of the overall growth and flowering habit of 'Balsursre'.
Figure 2:
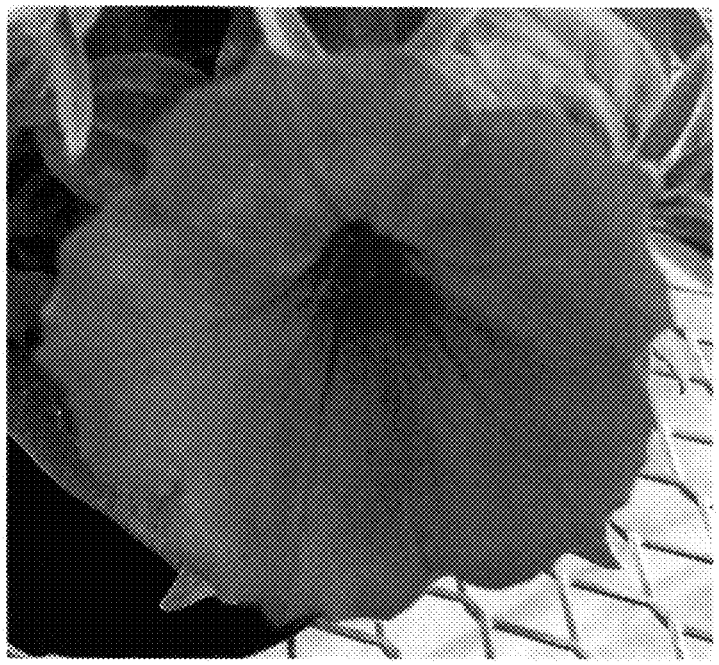
FIG. 2 illustrates a close-up view of an individual flower of 'Balsursre'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2022 under natural light conditions in Naperville, Ill.

The following descriptions and measurements describe approximately 11-week-old plants produced from cuttings from stock plants and grown in a polycarbonate greenhouse under conditions comparable to those used in commercial practice. The plants were grown in West Chicago, Ill. in 6-inch containers for approximately 8 weeks utilizing a soilless growth medium. Plants were given one pinch three weeks after transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Petunia* x *hybrida* 'Balsursre'.

Parentage:

*Female parent*.—Proprietary *Petunia* x *hybrida* breeding selection coded PET-00292-01, not patented.

*Male parent*.—Proprietary *Petunia* x *hybrida* breeding selection coded PET-00274-04, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 5 to 7 weeks from a rooted cutting to finish in a 10 cm container.

*Growth habit and general appearance*.—Moderately vigorous, mounded-trailing growth habit.

*Size*.—Height from soil level to top of plant plane: Approximately 19.0 cm. Width: Approximately 29.0 cm.

*Branching habit*.—Freely branching, pinching increases basal branching. Quantity of main branches per plant: Approximately 6.

*Branch*.—Strength: Moderate. Length: Approximately 15.5 cm. Diameter: Approximately 4.0 mm. Length of central internode: Approximately 1.7 cm. Texture: Densely glandular pubescent with a mixture of long and short hairs. Gland color: Colorless, transparent. Color of young stems:144A. Color of mature stems: 146B.

Foliage description:

*General description*.—Quantity of leaves per main branch: Approximately 10. Fragrance: Slight. Form: Simple. Arrangement on flowering stem: Alternate.

*Leaves*.—Aspect: Acute angle to stem. Shape: Ovate. Margin: Entire. Apex: Broadly acute. Base: Broadly attenuate. Venation pattern: Pinnate. Length of mature leaf: Approximately 7.0 cm. Width of mature leaf: Approximately 4.5 cm. Texture of upper and lower surfaces: Moderately glandular pubescent. Gland color: Colorless, transparent. Color of upper surface of young and mature foliage: 137A with venation of 146C to indistinguishable. Color of lower surface of young and mature foliage: Closest to 146B with venation of 146D to indistinguishable.

*Petiole*.—Length: Approximately 5.0 mm. Width: Approximately 3.0 mm. Texture: Moderately glandular pubescent with a mixture of long and short hairs. Gland color: Colorless, transparent. Color: 146D.

Flowering description:

*Flowering habit*.—'Balsursre' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 10. Fragrance: None detected.

*Bud*.—Rate of opening: Generally takes 2 to 3 days for bud to progress from first color to fully open flower. Quantity per plant: Approximately 6.

*Bud just before opening*.—Shape: Oblong. Length: Approximately 4.5 cm. Diameter at apex: Approximately 9.0 mm. Diameter at base: Approximately 2.0 mm. Texture: Densely glandular pubescent. Gland color: Colorless, transparent. Color of petal portion: Closest to but more grey than 186A with midveins of N77A. Color of tube: Closest to 183D with venation of 146B.

*Corolla*.—Diameter: Approximately 6.3 cm.

*Petals*.—Quantity: 5, fused to form a tube. Shape: Obovate. Appearance: Matte. Margin: Entire, slightly wavy. Apex: Cuspidate to rounded. Length from tube: Approximately 3.1 cm. Length of free portion: Approximately 1.1 cm. Width: Approximately 3.0 cm. Texture of upper surface: Glabrous. Texture of lower surface: Sparsely glandular pubescent. Gland color: Colorless, transparent. Color of upper surface when first and fully open: 45B to 45A with weakly colored midviens of N77A. Color of lower surface when first and fully open: Between 186B and 186C with midveins of 146B.

*Corolla tube*.—Length: Approximately 3.5 cm. Diameter at distal end: Approximately 1.0 cm. Diameter at proximal end: Approximately 2.0 mm. Texture of inner surface: Glabrous. Texture of outer surface: Densely glandular pubescent. Gland color: Colorless, transparent. Color of inner surface: 177A to 177B with venation of 200B. Color of outer surface: Closest to 183D with venation of 146B.

*Sepals*.—Quantity per flower: 5, fused at base. Shape: Linear. Margin: Entire. Apex: Acute. Length: Approximately 3.0 cm. Width: Approximately 5.0 mm. Texture of upper and lower surfaces: Densely glandular pubescent. Gland color: Colorless, transparent. Color of upper surface: 137A. Color of lower surface: 138A with 144A at base.

*Peduncle*.—Strength: Strong, flexible. Aspect: Acute angle to stem. Length: Approximately 3.5 cm. Diameter: Approximately 2.0 mm. Texture: Densely glandular pubescent with a mixture of long and short hairs. Gland color: Colorless, transparent. Color: 146B.

*Reproductive organs*.—Androecium: Stamen quantity: 5, basifixed. Stamen length: Approximately 2.6 cm. Filament length of fixed portion: Approximately 9.0 mm. Filament color: N155B. Anther shape: Bilobed. Anther length: Approximately 1.0 mm. Anther color: 158D. Pollen amount: Abundant. Pollen color: NN155A. Gynoecium: Pistil quantity: 1 per flower. Pistil length: Approximately 2.8 cm. Stigma shape: Funnel. Stigma length: Approximately 1.0 mm. Stigma color: 146A. Style length: Approximately 2.3 cm. Style color: 145D. Ovary length: Approximately 4.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balsursre', substantially as herein illustrated and described.

* * * * *